United States Patent
Kandel et al.

(10) Patent No.: US 10,159,970 B2
(45) Date of Patent: Dec. 25, 2018

(54) LONG CHAIN ALCOHOL

(71) Applicant: ExxonMobil Chemical Patents Inc., Baytown, TX (US)

(72) Inventors: Kapil Kandel, Humble, TX (US); Paul F. Keusenkothen, Houston, TX (US); Jeevan S. Abichandani, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/904,979

(22) Filed: Feb. 26, 2018

(65) Prior Publication Data
US 2018/0185830 A1  Jul. 5, 2018

Related U.S. Application Data

(62) Division of application No. 15/146,468, filed on May 4, 2016, now Pat. No. 9,931,621.

(60) Provisional application No. 62/167,514, filed on May 28, 2015.

(30) Foreign Application Priority Data

Sep. 1, 2015  (EP) .................................... 15183246

(51) Int. Cl.
| | |
|---|---|
| *C07C 29/156* | (2006.01) |
| *C07C 31/125* | (2006.01) |
| *B01J 35/10* | (2006.01) |
| *B01J 37/02* | (2006.01) |
| *B01J 23/745* | (2006.01) |
| *B01J 23/72* | (2006.01) |
| *B01J 8/02* | (2006.01) |

(52) U.S. Cl.
CPC .............. *B01J 35/1019* (2013.01); *B01J 8/02* (2013.01); *B01J 23/745* (2013.01); *B01J 35/1014* (2013.01); *B01J 35/1061* (2013.01); *B01J 37/0201* (2013.01); *C07C 29/156* (2013.01); *B01J 23/72* (2013.01); *B01J 2208/027* (2013.01)

(58) Field of Classification Search
CPC .... C07C 29/156; C07C 31/125; B01J 23/745; B01J 35/1019; B01J 8/02; B01J 35/1061; B01J 35/1014; B01J 2208/027
See application file for complete search history.

(56) References Cited

U.S. PATENT DOCUMENTS

| | | |
|---|---|---|
| 4,122,110 A | 10/1978 | Sugier et al. |
| 6,096,288 A | 8/2000 | Roth |
| 2004/0192989 A1 | 9/2004 | Espinoza et al. |
| 2005/0107481 A1 | 5/2005 | Janssen et al. |
| 2007/0259972 A1 | 11/2007 | Lattner et al. |
| 2008/0033218 A1 | 2/2008 | Lattner et al. |

OTHER PUBLICATIONS

Bao et al., higher alcohol synthesis over Cu—Fe composite oxides with high selectivity to C2+OH, (Journal of Energy Chemistry 22 (2013) 107-113).*
Cao et al., "Mesoporous CuO—Fe2O3 composite catalysts for low-temperature carbon monoxide oxidation", Applied Catalysis B: Environmental, vol. 79, (2008) pp. 26-34.
Frennet, et al., "Long-chain alcohols from syngas", In Studies in Surface Science and Catalysis, A. Corma, F.V.Melo, S. Mendioroz and J.L.G. Fierro, Eds., Elsevier Science 2000, vol. 130, pp. 3699-3704.
Xiang et al., "Long-Chain Terminal Alcohols through Catalytic CO Hydrogenation", Journal of the American Chemical Society, 2013, vol. 135, pp. 7114-7117.
Beck J.S., et al., J. Am. Chem. Soc., vol. 114, No. 127, 10834-10843 (1992).
Cao, at al., J. Mater. Sci. (2009) 44:6663-6669.
Guilong et al. "Nanoparticles of Cu—Co Alloy Supported on High Surface Area LaFeO 3—preparation and catalytic performance for higher alcohol synthesis from syngas", RSC Advances: An International Journal to Further the Chemical Sciences, vol. 5, No. 40, Mar. 26, 2015 pp. 31637-31647.
Jiao F., et al., J. Mater. Chem. A, 2, 3065-3071 (2014).
Liu Q., et al., Microporous and Mesoporous Materials, 100, 233-240 (2007).
Lu, et al., ChemCat Chem 2014, 6, 473-478.
Lu, et al., Applied Catalysis A: General 429-430 (2012).
Maerle et al. "Structured mesoporous Mn, Fe, and Co oxides: Synthesis, Physiochemical, and Catalytic Properties", Russian Journal of Physical Chemistry A., vol. 88, No. 2, Feb. 1, 2014, pp. 238-242.
Sakamoto, et al., Nature, 408, 449-452 (2000).
Schwickardi M. et al. "High Surface-Area Oxides Obtained by an Activated Carbon Route", Chemistry of Materials, American Chemical society, US. vol. 14, No. 9, Sep. 1, 2002, pp. 3913-3919.
Yoshimura T., et al., Langmuir 28, 9322-9331 (2012).
Gao et al., "Catalytic conversion of syngas to mixed alcohols over CuFe based catalyst derived from layered double hydroxides", Catalysis Science and Technology, 2013, vol. 3, pp. 1324-1332.

* cited by examiner

Primary Examiner — Jafar F Parsa

(57) ABSTRACT

The invention relates to long chain alcohol, to processes for catalytically producing long chain alcohol from carbon monoxide and molecular hydrogen, to equipment useful in such processes, and to the use of long chain alcohol, e.g., for producing fuel, lubricating oil, detergent, and plasticizer. The catalyst is mesoporous and comprises iron and copper.

8 Claims, No Drawings

LONG CHAIN ALCOHOL

PRIORITY

This application is a divisional of and claims priority to and the benefit of U.S. patent application Ser. No. 15/146,468, filed May 4, 2016, U.S. Patent Application Ser. No. 62/167514,filed May 28, 2015, and European Patent Application No. 15183246.6 filed Sep. 1, 2015, all of which are herein incorporated by reference. The following related cases are also incorporated by reference in their entireties: U.S. Provisional Patent Application Ser. No. 62/167525, filed May 28, 2015 and European Patent Application No. 15177842.0 filed Jul. 22, 2015.

FIELD OF THE INVENTION

The invention relates to long chain alcohol, to processes for catalytically producing long chain alcohol from carbon monoxide and molecular hydrogen, to equipment useful in such processes, and to the use of long chain alcohol, e.g., for producing fuel, lubricating oil, detergent, and plasticizer.

BACKGROUND OF THE INVENTION

Many commercially important compositions, including fuel, lubricating oil, detergent, and plasticizer compositions, contain or are produced using long chain alcohol (unbranched $C_{4+}$ alcohol having one terminal hydroxyl). Butanol, for example, can be used to produce butyl acrylate and methacrylate. $C_5$ alcohol can be used to produce lubricating oil additives such as zinc diamyldithiophosphate. Alcohols in the $C_6$-$C_9$ range can be used to produce plasticizer. $C_6$-$C_9$ alcohol, particularly $C_{12}$-$C_{15}$ alcohol, can be used to produce detergent, typically by first converting the alcohol to alcohol sulfate, ethoxylate, alcohol ether sulfate, or fatty amine.

One way to produce long chain alcohol is by catalytic hydroformylation of olefin. The hydroformylation reaction produces a reaction product comprising aldehyde. Linear aldehyde is separated from the reaction product. Alcohol is produced by hydrogenating the separated linear aldehyde. The hydroformylation reaction is carried out by contacting the olefin with a mixture of carbon monoxide and molecular hydrogen in the presence of at least one hydroformylation catalyst. Conventional hydroformylation catalysts typically comprise at least one metal selected from Groups 8-10 of the Periodic Table, especially at least one metal selected from Group 9, such as one or more of cobalt, rhodium, and iridium. Although rhodium and iridium exhibit greater hydroformylation activity, cobalt is typically used to lessen costs. When using a cobalt catalyst such as $HCo(CO)_4$, hydroformylation conditions typically include a temperature ≥140° C. and a pressure ≥24 MPa. Relatively high pressure is needed for at least two reasons. First, high total pressure is needed to stabilize the catalyst at the reaction temperature. Second, selectivity for the desired linear aldehyde over branched aldehyde by-product increases with increasing carbon monoxide partial pressure.

Besides needing relatively high temperature and pressure, conventional hydroformylation processes are also sensitive to the type of olefin present in the feed. Linear olefin is approximately an order of magnitude more reactive for producing the desired aldehyde than is iso-olefin having the same number of carbon atoms. Consequently, conventional hydroformylation processes typically require concentrating linear olefin in the feed, e.g., by separating and conducting away any isoolefin. In addition to these difficulties, catalysts such as $HCo(CO)_4$ have a normal boiling point similar to that of desirable linear aldehydes, which increases the complexity of product and catalyst recovery stages.

In order to more easily recover catalyst from the long-chain alcohol, processes have been developed to produce long chain alcohol by direct hydration of 1-alkene using acids, metal oxides, zeolites, or clays. One difficulty in operating these processes results from an aspect of Markovnikov's rule: a proton bonds to a hydrocarbon molecule at the molecule's least-substituted carbon atom. Accordingly, the hydration reaction protonates the 1-alkene's double bond, which disfavors transition states amenable to long chain alcohol formation. Although triple-relay, platinum-ruthenium catalyst systems having anti-Markovnikov behavior have been developed for 1-alkene hydration, a more recent approach involves the direct production of long chain alcohol by a modified Fischer-Tropsch ("FT") synthesis.

As reported in Lu, et al., ChemCatChem 2014, 6, 473-478, processes using modified Cu—Fe FT synthesis catalysts can be operated to strongly favor producing long chain alcohol (anti-Markovnikov behavior) from a carbon monoxide–molecular hydrogen mixture over producing branched alcohol having the same number of carbon atoms (Markovnikov behavior). The reference discloses reacting a 1:1 molar ratio carbon monoxide–molecular hydrogen mixture in the presence of a three-dimensional, ordered macroporous catalyst comprising CuO and $Fe_3O_4$. The reaction is carried out at a temperature of 240° C. and a pressure of 700 psi (approximately 4.8 Mpa). The reference discloses a selectivity to $C_{2+}$ 1-alcohol production of 40% (weight basis) and a feed carbon monoxide conversion of 45% (weight basis). 1-alcohol in the reaction product have a number of carbon atoms in the range of from 1 to 16, with a weight average of about 9, resulting in an Anderson-Shulz-Flory Chain Growth Probability ("α") of 0.74.

Processes are now desired for catalytically producing long chain alcohol from a carbon monoxide—molecular hydrogen mixture, the process having one or more of (i) a feed carbon monoxide conversion >45% (weight basis), (ii) 1-alcohol selectivity >40% (weight basis), and (iii) an α>0.74. Such processes as can be carried out at a reaction temperature ≤250° C. and a total pressure ≤5 Mpa are particularly desired.

SUMMARY OF THE INVENTION

In certain aspects, the invention relates to a process for producing long chain alcohol from a feed mixture which includes carbon monoxide and molecular hydrogen. The process can be carried out a reaction temperature ≤250° C. and a total pressure ≤5 Mpa, and can exhibit one or more of (i) a feed carbon monoxide conversion >45% (weight basis), (ii) 1-alcohol selectivity >40% (weight basis), (iii) α>0.74.

The invention is based in part on the discovery of mesoporous active materials having increased activity and selectivity for long chain alcohol production over conventional alcohol synthesis catalysts. The active materials comprise copper and iron, and have a surface area ≥50 $m^2/g$.

Accordingly, certain aspects the invention relate to a process for producing long chain alcohol from a feed mixture comprising molecular hydrogen and ≥0.01 wt. % of carbon monoxide, wherein the feed mixture has a molecular hydrogen to carbon monoxide molar ratio in the range of from 0.01 to 100. The feed mixture's carbon monoxide and molecular hydrogen are reacted in the presence of at least one catalyst. The reaction is carried out at a temperature ≥150° C., a total pressure ≥0.8 MPa (about 100 psig), and a space velocity (GHSV)≥100 hr$^{-1}$. The catalyst comprises copper, ≥0.5 wt. % of iron, ≤1.0 wt. % of CuO and ≤1.0 wt. % of Fe$_3$O$_4$. The catalyst has an iron to copper molar ratio in the range of from 0.1 to 10, a plurality of pores having an average pore size in the range of from 2 nm to 50 nm; and an average surface area ≥50 m$^2$/g. The reaction effluent comprises any unreacted feed mixture and a reaction product which includes long chain alcohol. In processes for making long chain alcohol from syngas, the macroporous catalysts disclosed in the Lu reference have improved performance over microporous catalysts, which in turn exhibit improved performance over non-porous catalysts. Since this indicates a positive correlation between catalyst pore size and long chain alcohol synthesis, it is surprising that the mesoporous catalysts of the invention exhibit improved performance over macroporous catalysts.

Other aspects of the invention relate to a multi-metallic composition, comprising copper, ≥0.5 wt. % of iron, ≤1.0 wt. % of CuO and ≤1.0 wt. % of Fe$_3$O$_4$. The multi-metallic composition has an iron to copper molar ratio in the range of from 0.1 to 10, a plurality of pores having an average pore size in the range of from 2 nm to 50 nm, and an average surface area ≥50 m$^2$/g.

Other aspects of the invention relate to an apparatus for producing long chain alcohol. The apparatus comprises at least one reactor vessel, the reactor vessel having an internal volume which includes an upstream region and a downstream region. The apparatus includes at least one feed conduit in fluidic communication with a syngas source located upstream of the reactor vessel and the reactor vessel's interior volume. The feed conduit is configured to establish a flow of syngas from the syngas source to the upstream region of the reaction vessel's interior volume. The apparatus also includes at least one reaction zone. The reaction zone is located between the upstream and downstream regions of the reactor vessel's interior volume, and is configured to receive the syngas flow from the upstream region of the reactor's interior volume and to discharge a reaction effluent flow comprising the long chain alcohol into the downstream region of the reaction vessel's interior volume. The reaction zone contains at least one bed of a multi-metallic, mesoporous catalyst. The catalyst comprises copper, ≥0.5 wt. % of iron, ≤1.0 wt. % of CuO and ≤1.0 wt. % of Fe$_3$O$_4$, and has an iron to copper molar ratio in the range of from 0.1 to 10. The catalyst has a plurality of pores having an average pore size in the range of from 2 nm to 50 nm, and an average surface area ≥50 m$^2$/g. The apparatus produces long chain alcohol by a reaction of syngas in the syngas flow in the presence of the catalyst. The apparatus also includes at least one product conduit in fluidic communication with the downstream region of the reactor vessel's interior volume and a recovery stage located downstream of the reactor vessel. The product conduit is configured to conduct the reaction effluent flow from the downstream region of the reactor vessel's interior volume to the recovery stage, the recovery stage being configured to recover at least a portion of the long chain alcohol.

DETAILED DESCRIPTION OF THE INVENTION

Definitions

For the purpose of this description and appended claims, the following terms are defined:

The term "$C_n$" hydrocarbon means hydrocarbon having n carbon atom(s) per molecule, wherein n is a positive integer.

The term "$C_{n+}$" hydrocarbon means hydrocarbon having at least n carbon atom(s) per molecule, wherein n is a positive integer. The term "$C_{n-}$" hydrocarbon means hydrocarbon having no more than n number of carbon atom(s) per molecule, wherein n is a positive integer. The term "hydrocarbon" means a class of compounds containing hydrogen bound to carbon, and encompasses (i) saturated hydrocarbon, (ii) unsaturated hydrocarbon, and (iii) mixtures of hydrocarbons, including mixtures of hydrocarbon compounds (saturated and/or unsaturated), including mixtures of hydrocarbon compounds having different values of n.

The term "$C_n$" alcohol means alcohol having n carbon atom(s) per molecule, wherein n is a positive integer. The term "$C_{n+}$" alcohol means alcohol having at least n carbon atom(s) per molecule, wherein n is a positive integer. The term "$C_{n-}$" alcohol means alcohol having no more than n number of carbon atom(s) per molecule, wherein n is a positive integer. The term "alcohol" means a class of compounds which include at least one aliphatic carbon bound to a hydroxyl group, but excluding aldehyde, ketone, and carboxylic acid. The term alcohol encompasses (i) saturated and unsaturated alcohol, (ii) alcohol having one hydroxyl group per alcohol molecule (mono-alcohol) and alcohol having a plurality of hydroxyl groups per alcohol molecule (di-alcohol, tri-alcohol, etc.), (iii) primary, secondary, and tertiary alcohol, (iv) alcohol having a terminal hydroxyl group (1-alcohol) and alcohol having a hydroxyl group in a non-terminal position (2-alcohol, 3-alcohol, etc.), and (iv) mixtures of two or more alcohol compounds, including mixtures of alcohol compounds having different values of n.

The term "long chain alcohol" means a class of saturated, primary, mono-alcohol compounds having (i) the form of a single unbranched chain which includes four or more carbon atoms, the chain beginning with a first terminal carbon atom and ending with a second terminal carbon atom, (ii) each of the chain's non-terminal carbon atoms tetravalently bound to two nearest-neighbor hydrogen atoms and to two nearest-neighbor carbon atoms of the chain, and (iii) a sole hydroxyl group, the sole hydroxyl group and two hydrogen atoms each being directly bound to the first terminal carbon atom, the second terminal carbon atom being directly bound to three hydrogen atoms (namely: normal, $C_{4+}$, saturated, primary, mono-, 1-alcohol). Typically, the number of carbon atoms in the single unbranched chain is in the range of from 5 to 21, more typically in the range of from 5 to 15, e.g., in the range of from 6 to 12.

The term "alkane" means substantially-saturated compounds containing hydrogen and carbon only, e.g., those containing ≤1% (molar basis) of unsaturated carbon atoms. As an example, the term alkane encompasses $C_2$ to $C_{20}$ linear, iso, and cyclo-alkanes.

The term "unsaturate" or "unsaturated hydrocarbon" mean a $C_2$+hydrocarbon containing at least one carbon atom directly bound to another carbon atom by a double or triple bond. The term "olefin" means an unsaturated hydrocarbon containing at least one carbon atom directly bound to another carbon atom by a double bond. In other words, an olefin is a compound which contains at least one pair of carbon atoms, where the first and second carbon atoms of the pair are directly linked by a double bond.

The term "Periodic Table" means the Periodic Chart of the Elements, as it appears on the inside cover of The Merck Index, Twelfth Edition, Merck & Co., Inc., 1996.

The term "reaction zone" or "reactor zone" means a location within a reactor, e.g., a specific volume within a reactor and/or a specific volume between two reactors for carrying out a reaction which produces alcohol. The term "fixed bed catalytic reactor" means a catalytic reactor having at least one bed of catalyst, wherein the catalyst is substantially retained within the bed and remains in a substantially fixed location within the bed.

The term "selectivity" refers to the production of a specified compound in a catalytic reaction. As an example, the phrase "the reaction has a 100% selectivity for 1-alcohol" means that the reaction produces 100% 1-alcohol. When used in connection with a specified reactant, the term "conversion" means the amount of the reactant consumed in the reaction. For example, when the specified reactant is CO, 100% conversion means 100% of the CO is consumed in the reaction.

Certain aspects the invention relate to a process for catalytically producing long chain alcohol from a feed mixture comprising carbon monoxide and molecular hydrogen. Typical feed mixtures will now be described in more detail. The invention is not limited to these feed mixtures, and this description is not meant to foreclose the use of other feed mixtures within the broader scope of the invention.

Feed Mixture

The feed mixture comprises molecular hydrogen and carbon monoxide, e.g., ≥0.01 wt. % carbon monoxide based on the weight of the feed mixture, such as ≥1 wt. %, and has a molecular hydrogen to carbon monoxide molar ratio in the range of from 0.01 to 100. The feed mixture typically comprises ≥5 wt. % carbon monoxide and optionally further comprises diluent such as carbon dioxide. For example, the feed mixture can comprise 5 wt. % to 95 wt. % of carbon monoxide, and can have a molecular hydrogen molar ratio in the range of from 0.25 to 20, e.g., 0.25 to 20, such as 0.5 to 20. Such mixtures are typically referred to as synthesis gas (or "syngas"). In certain aspects, the feed mixture includes syngas comprising molecular hydrogen, ≥10 wt. % carbon monoxide, and diluent. The diluent typically comprises carbon dioxide. The syngas typically has an $H_2$:$(CO+CO_2)$ molar ratio in the range of from 0.25 to 20, or 0.5 to 20, e.g., an $H_2$:CO ratio in the range of from 0.25 to 20, or 0.5 to 20. Certain suitable syngas mixtures have an $H_2$:CO molar ratio in the range of from 0.25 to 4.

The syngas can be produced from a carbon-containing source material, such as hydrocarbon, e.g., hydrocarbon in the form of one or more of natural gas, petroleum, coal, biomass, including mixtures thereof, derivatives thereof, and mixtures of such derivatives. The type of carbon-containing source material used is not critical. The source material typically comprises ≥10 vol. %, such as ≥50 vol. %, based on the volume of the source material, of at least one hydrocarbon, especially methane.

Any convenient method for producing syngas can be used, including conventional methods. Suitable methods include those described in U.S. Patent Application Publications Nos. 20070259972 A1; 20080033218 A1; and 20050107481, each of which is incorporated by reference herein in its entirety. For example, natural gas can be converted to syngas by steam reforming. The first step normally involves the removal of inert components in the natural gas, such as nitrogen, argon, and carbon dioxide. Natural gas liquids will also be recovered and directed to other processing or transport. The treated natural gas will comprise primarily methane and some ethane with small amounts of higher alkanes, such as propane. Preferably, the natural gas comprises more than 90 vol. % methane. The treated natural gas is then contacted with steam in the presence of a catalyst, such as one or more metals or compounds thereof selected from Groups 7 to 10 of the Periodic Table supported on at least one attrition-resistant refractory support, such as alumina. The contacting is normally conducted at high temperature, such as in the range of from 800° C. to 1100° C., and pressures ≤5000 kPa. Under these conditions, methane converts to carbon monoxide and hydrogen according to reactions, such as:

$$CH_4+H_2O \rightarrow CO+3H_2.$$

Steam reforming is energy intensive in that the process consumes over 200 kJ/mole of methane consumed. A second method is partial oxidation, in which the methane is burned in an oxygen-lean environment. The methane is partially-oxidized to carbon monoxide (reaction (i)), with a portion of the carbon monoxide being exposed to steam reforming conditions (reaction (ii)) to produce molecular hydrogen and carbon dioxide, according to the following representative reactions:

$$CH_4+3/2O_2 \rightarrow CO+2H_2O \text{ (i)},$$

$$CO+H_2O \rightarrow CO_2+H_2 \text{ (ii)}.$$

Partial oxidation is exothermic and yields a significant amount of heat. Because one reaction is endothermic and the other is exothermic, steam reforming and partial oxidation are often performed together for efficient energy usage. Combining the steam reforming and partial oxidation yields a third process wherein the heat generated by the partial oxidation is used to drive the steam reforming to yield syngas.

The feed mixture, typically syngas, is reacted in the presence of at least one multi-metallic mesoporous catalyst to produce long chain alcohol. The catalyst will now be described in more detail.

Multi-metallic, Mesoporous Catalyst

The multi-metallic, mesoporous catalyst comprises copper, ≥0.5 wt. % of iron, ≤1.0 wt. % of CuO and ≤1.0 wt. % of $Fe_3O_4$, and has an iron to copper molar ratio in the range of from 0.1 to 10. The catalyst has a plurality of pores having an average pore size in the range of from 2 nm to 50 nm; and has an average surface area ≥50 $m^2/g$.

The catalyst is multi-metallic in that it comprises copper and iron. While not wishing to be bound by any theory or model, it is believed that the copper provides the catalyst with alcohol synthesis functionality and the iron provides the catalyst with Fischer-Tropsch synthesis (carbon atom chain growth) functionality. The catalyst is mesoporous in that it has a plurality of pores, the pores having an average pore size in the range of from 2 nm to 50 nm. When the catalyst is in the form of a particulate, typically each catalyst particle has a plurality of pores having an average pore size in the specified range. While not wishing to be bound by any theory or model, it is believed that an average pore size in the specified range favors the formation of long chain alcohols over alcohol having three or fewer carbon atoms. The catalyst has an average surface area ≥50 $m^2$ per gram of catalyst. Conventional methods can be utilized for determining (i) the type, amount, electronic structure, and physical structure of catalyst components, e.g., those of iron and copper, (ii) average pore size, (iii) average surface area, (iv) the amount of order, if any, exhibited by the plurality of pores and the boundaries thereof, and (v) catalyst morphology (including the size and shape of catalyst particles when the catalyst is at least partly in the form of particulates). For example, the amounts of iron and copper can be determined using energy-dispersive mapping methods disclosed in Y. Lu, et al., Applied Catalysis A: General 429-430 (2012). Catalyst morphology can be determined using SEM and TEM methods disclosed in this article. X-ray diffraction methods disclosed in this article can be used for deterring the physical structure (and phases) of metals, including iron and copper, present in the catalyst, and can also for determining catalyst particle size. Average surface area, average pore size, and pore size distribution can be determined using $N_2$ adsorption/desorption methods disclosed in Cao, at al., J. Mater. Sci. (2009) 44:6663-6669. The amount of mesoporous order, if any, exhibited by the pores can be determined using x-ray diffraction methods disclosed in J. S. Beck, et al., J. Am. Chem. Soc., Vol. 114, No. 127, 10834-10843 (1992). Should the catalyst have insufficient mesoporous order to exhibit diffraction peaks at a scattering angle $2\theta \leq 4°$ when utilizing the x-ray scattering methods of the J. Am. Chem. Soc. article, average pore size and the amount of ordered mesoporosity (if any) can be determined using the direct HREM imaging methods disclosed in Sakamoto, et al., Nature, 408, 449-452 (2000). The electronic structure of catalyst components such as copper and iron can be determined using photoemission methods including XPS and Auger Electron Spectroscopy methods disclosed in Y. Lu et al., ChemCatChem 6, 473-476 (2014), which is incorporated by reference herein in its entirety.

Typically, the catalyst comprises copper in an amount in the range of 0.75 wt. % to 50.0 wt. %, based on the weight of the catalyst, more typically in the range of 1.0 wt. % to 10 wt. %. Typically, the amount of iron is in the range of from 0.75 wt. % to 50.0, based on the weight of the catalyst, more typically in the range of from more typically in the range of 1.0 wt. % to 10 wt. %. In certain aspects, the catalyst has an iron to copper molar ratio in the range of from 0.25 to 4.

All or a portion of the iron can be located in the catalyst, e.g., comprising a catalyst framework which separates nearest-neighbor pores ("framework iron"). In certain aspects, at least a portion of the iron is located on the surface of the catalyst ("surface iron"), e.g., iron located at or proximate to catalyst pore openings and/or inside the pores. The iron (surface iron and/or framework iron) can be, e.g., in one or more metallic iron phases (iron atoms bound to neighboring iron atoms) and/or in one or more carbide phases such as $FeC_2$. All or a portion of the copper can be located in the catalyst, e.g., comprising a catalyst framework which separates nearest-neighbor pores ("framework copper"). In certain aspects, at least a portion of the copper is located on the surface of the catalyst ("surface copper"), e.g., copper located at or proximate to catalyst pore openings and/or inside the pores. The copper (surface copper and/or framework copper) can be, e.g., in one or more metallic copper phases (copper atoms bound to neighboring copper atoms) and/or in one or more carbide phases such as $CuC_2$. Typically, the metallic and carbide phases of iron and/or copper are substantially crystalline (e.g., substantially polycrystalline), but this is not required. Typically, $\geq 50.0$ wt. % of the iron is framework iron, e.g., $\geq 75.0$ wt. %, based on the weight of the catalyst, such as $\geq 90.0$ wt. %, or in the range of from 50.0 wt. % to 100.0 wt. %, or 75.0 wt. % to 99.0 wt. %. Typically, $\geq 50.0$ wt. % of the copper is surface copper, e.g., $\geq 75.0$ wt. %, based on the weight of the catalyst, such as $\geq 90.0$ wt. %, or in the range of from 50.0 wt. % to 100.0 wt. %, or 75.0 wt. % to 99.0 wt. %.

Besides copper and iron, the catalyst can further comprise additional materials, e.g. a third metal (which can be a mixture of metals). When present, the amount of third metal can be $\leq 10.0$ wt. %, e.g., in the range of about 0.1 wt. % to about 10.0 wt. %, or about 0.5 wt. % to about 5 wt. %. The third metal can include, for example, one or more of Mn, Zn, Rh, and Co. The third metal can be located on the catalyst surface (on internal and/or external surfaces as "surface metal"). Instead or in addition, the third metal can be located in the catalyst's framework ("framework metal"). Besides or in addition to the third metal, the catalyst can further comprise other material, such as carbon (including surface carbon and/or framework carbon), e.g., carbon introduced during synthesis of a catalyst precursor. Carbon can also accumulate on the precursor and/or catalyst during precursor processing, e.g., when the catalyst is produced from the precursor by exposing the precursor to reducing conditions in the presence of a reducing agent such as syngas. Carbon can also accumulate on the catalyst when it is present during the conversion of a carbon monoxide+molecular hydrogen mixture to long chain alcohol. When the catalyst includes carbon, the catalyst typically comprises $\leq 95$ wt. % carbon, based on the weight of the catalyst, e.g., $\leq 90$ wt. %, such as in the range of from 1 wt. % to 90 wt. %, or 10 wt. % to 85 wt. %. When present, the carbon is typically in the form of one or more of (i) carbonaceous deposits, such as coke and/or soot deposits, (ii) carbonaceous layers, e.g., graphitic carbon layers, and (iii) metal carbide, e.g., $FeC_2$, $CuC_2$, etc. When present, coke/soot deposits and carbonaceous layers are typically located on and/or in the catalyst, e.g., in catalyst pores, e.g., as coke particles. When present, metal carbides can be located on and/or in the catalyst, e.g., as carbide particulates on the catalyst surface and/or in the catalyst pores. Metal carbide can also be a component of the catalyst framework, e.g., when the catalyst framework comprises iron.

The catalyst comprises $\leq 1.0$ wt. % of CuO and $\leq 1.0$ wt. % of $Fe_3O_4$. Typically, the catalyst comprises $\leq 0.5$ wt. % of CuO and/or $\leq 0.5$ wt. % of $Fe_3O_4$, e.g., $\leq 0.1$ wt. % of CuO and/or $\leq 0.1$ wt. % of $Fe_3O_4$, such as in the range of 0.05 wt. % CuO to 1.0 wt. % CuO and/or in the range of 0.05 wt. % $Fe_3O_4$ to 1.0 wt. % $Fe_3O_4$. In certain aspects, the catalyst is substantially free of any oxide of copper (e.g., CuO, $Cu_2O$, etc.) and/or substantially free of any oxide of iron (e.g., $Fe_3O_4$, $Fe_2O_3$, etc.). The term "substantially free" in this context means $\leq 0.05$ wt. % based on the weight of the catalyst. When the catalyst is produced from one or more precursors which contain CuO and/or $Fe_3O_4$, the method for producing the catalyst from the precursor typically includes a step for reducing these oxides, e.g., by exposing the precursor to a reducing gas such as syngas under conditions effective for reducing the catalyst. Typically, the catalyst comprises $\leq 15.0$ wt. % of oxygen atoms, based on the weight of the catalyst, whether as unbound oxygen ions, oxygen atoms bound to at least one other oxygen atoms, oxygen atoms bound to at least one hydrogen atoms, and/or oxygen atoms bound to at least one of copper (oxide of copper) and iron (oxide of iron). More typically, the catalyst comprises $\leq 10.0$ wt. % of oxygen atoms, e.g., $\leq 1.0$ wt. %, such as in the range of 0.1 wt. % to 10.0 wt. %, or 0.5 wt. % to 5.0 wt. %.

The catalyst comprises a plurality of pores having an average pore size in the range of from 2 nm to 50 nm; and an average surface area $\geq 50$ m$^2$/g. Typically, the average pore size is in the range of from 4 nm to 25 nm, and the average surface area is in the range of 50 m$^2$/g to 350 m$^2$/g, such as from 60 m$^2$/g to 250 m$^2$/g. Although at least some pores in the specified size range can exhibit a substantially regular order (an "ordered mesoporous catalyst"), this is not required, and in certain aspects the catalyst includes at least some disordered mesoporous catalyst, namely catalyst having few or no pores of the specified average size that are arranged in regular order. Disordered catalysts can include non-crystalline or poorly-crystalline framework material, but typically has a substantially crystalline (e.g., substantially polycrystalline) framework. Examples of ordered mesoporous materials appear in F. Jiao, et al., J. Mater. Chem. A, 2, 3065-3071 (2014) and examples of disordered mesoporous materials appear in the Microporous and Mesoporous Materials article. For the purpose of this description and appended claims, the terms "ordered" and "disordered" have the same meanings as used in those articles.

The catalyst can be a component of a catalyst system, e.g., one component of a catalyst composite. Besides catalyst, such a catalyst system or composite can further comprise one or more inorganic oxides, e.g., one or more of silica, alumina, magnesia, zirconia, oxide of zinc, etc. Such oxides can be present in the catalyst system as binder and/or catalyst support material, for example.

Multi-metallic, Mesoporous Catalyst Synthesis

The multi-metallic, mesoporous catalyst is typically synthesized using at least one structure-directing agent, typically called a "template". For example, a template can be used to produce a calcined multi-metallic templated precursor, which is then reduced to produce the catalyst. Synthesis methods utilizing one or more templates will now be described in more detail.

Suitable templates include, e.g., (i) ordered mesoporous inorganic materials such as one or more of MCM-41, MCM-48, SBA-15, KIT-6-100, and KIT-6-40 ("hard templating") and/or (ii) carbonaceous material, e.g., hydrocarbonaceous material, such as one or more of siloxane, urea, and surfactant ("soft templating").

Producing a Calcined Multi-metallic Templated Precursor from a Hard Template

In certain aspects, the catalyst is produced from a hard template comprising oxide of silicon, e.g., MCM-41. Conventional methods can be utilized for producing the template, such as the methods disclosed in U.S. Pat. No. 6,096,288 and in J. S. Beck, et al., J. Am. Chem. Soc., Vol. 114, No. 127, 10834-10843 (1992), which are incorporated by reference herein in their entireties. A metal-substituted template is produced by substituting a first metal, e.g., copper and/or iron, for at least a portion of the silicon atoms in the template's framework. Conventional methods can be used for carrying out the substitution, such as those which include heating a mixture of (i) hexane, (ii) copper nitrate and/or iron nitrate, and (iii) mesoporous silica template to a temperature of 70° C. for 20 hours. Suitable methods are disclosed in the J. Mater. Chem. A. article, which is incorporated by reference herein in its entirety. The metal-substituted template is recovered, e.g., by vacuum filtration.

The recovered metal-substituted template is calcined to produce a monometallic templated precursor. e.g., by exposing the metal-substituted template to an oxidant at a temperature ≥350° C. Conventional recovery and calcining conditions can be used, such as those disclosed in the J. Mater. Chem. A. article, but the invention is not limited thereto. Although the metal substation can be carried out under conditions which result in the substation of metal for substantially all of the template's silica, this is not required. Optionally, at least a portion of any silica in the monometallic templated precursor is removed, e.g., ≥90.0 wt. % of any silica based on the weight of the monometallic templated precursor. Silica removal can be carried out by conventional methods, such as by exposing the metal-substituted template to a 2M solution of NaOH at a temperature of approximately 25° C., but the invention is not limited thereto. Suitable silica removal methods are disclosed in the J. Mater. Chem. A. article, for example.

Following calcination, a multi-metallic templated precursor is produced by depositing a second metal on and/or in the monometallic templated precursor, e.g., depositing on the monometallic templated precursor's external surface and/or impregnating in the pores of the monometallic templated precursor. When the first metal is iron, the second metal is typically copper. When the first metal is copper, the second metal is typically iron. In certain aspects, the first metal is iron and the second metal is copper. Typically, the amount of second metal deposited on and/or in the monometallic templated precursor is selected to achieve a molar ratio of first to second metal in the in the range of from 0.1 to 10, e.g., about 0.25 to 4. Conventional methods can be used for impregnating the second metal, e.g., by exposing the monometallic templated precursor to an impregnation solution containing nitrate of the second metal, but the invention is not limited thereto. Optionally, the impregnation solution further comprises nitrate of the third metal. Suitable impregnation methods are disclosed, e.g., in J.-L. Cao, et al., J. Mater. Sci., 44, 6663-6669 (2009), which is incorporated by reference herein in its entirety. The multi-metallic templated precursor is calcined, e.g., by exposure to an oxidant at a temperature ≥350° C. Conventional calcining conditions can be used, such as those disclosed in the J. Mater. Chem. A and J. Mater. Sci. articles. Typically calcination of iron oxide (e.g., the first and/or second calcination as the case may be) is carried out under conditions to oxidize any $Fe_2O_3$ to $Fe_3O_4$.

In alternative aspects, co-impregnation and/or co-deposition of the first and second metal is carried out, the relative amount of first and second metal deposited on and/or impregnated in the template is selected to achieve a molar ratio of first to second metal in the multi-metallic templated precursor in the range of from 0.1 to 10, e.g., about 0.25 to 4. Co-impregnation can simplify catalyst production because the second calcining step is not needed.

Producing a Calcined Multi-metallic Templated Precursor from a Soft Template

In certain aspects, the catalyst is produced from a soft template by reacting at least one carbonaceous structure-directing agent and nitrate of a first metal to produce a mesoporous oxide template. A mono-metallic templated precursor is then produced by calcining the mesoporous oxide template. A multi-metallic templated precursor is produced by depositing a second metal on and/or in the monometallic templated precursor, e.g., on the monometallic templated precursor's external surface and/or in the pores of the monometallic templated precursor. When the first metal is iron, the second metal is typically copper. When the first metal is copper, the second metal is typically iron. In certain aspects, the first metal is iron and the second metal is copper. The multi-metallic templated precursor is calcined and reduced to produce the catalyst.

The structure-directing agent is typically one or more of siloxane, polymeric glycol, urea, and surfactant, more typically surfactant. The surfactant can be an individual surfactant compound, or a mixture of individual surfactant compounds, but is typically an individual surfactant compound. The surfactant can include one or more of cationic surfactant, non-ionic surfactant, zwitterionic surfactant, and anionic surfactant, but is typically cationic. The surfactant can comprise unbranched surfactant, e.g., cetyltrimethylammonium bromide. Alternatively or in addition, the surfactant can comprise branched surfactant, such as quaternary ammonium surfactant including those having at least one alkyl spacer; oligomeric quaternary ammonium surfactant including those having (i) at least one polar spacer such as at least one hydroxyl group and/or (ii) at least one aromatic (including alkyl aromatic) spacer group; dimeric surfactant including gemini surfactant and/or dimeric surfactant which includes siloxane; trimeric surfactant including (i) polyoxyethylene ether trimeric quaternary ammonium surfactant, (ii) polyoxyethylene trimeric surfactant, (iii) ring-type trimeric surfactant, (iv) trimeric surfactant derived from amine, and (v) n-alkylphenol polyoxyethylene trimeric surfactant; tetrameric surfactant; tetrameric surfactant, including those having at least one ring spacer; star-shaped trimeric tetrameric, and hexameric quaternary ammonium surfactant, including those having at least one amide group; and tyloxopol. Conventional surfactant can be used, but the invention is not limited thereto. Examples of suitable gemini surfactants are disclosed in Sakamoto, et al., Nature, 408, 449-452 (2000), which is incorporated by reference herein in its entirety. Examples of suitable trimeric surfactants are disclosed in T. Yoshimura, et al., Langmuir 28, 9322-9331 (2012), which is incorporated by reference herein in its entirety.

In certain aspects, a mesoporous oxide template is produced by combining a structure-directing agent, e.g., surfactant, and nitrate of a first metal, e.g., $Fe(NO_3)_3$, water, and optionally urea to produce a synthesis mixture. The synthesis mixture is then aged to produce mesoporous oxide template, e.g., by exposing the mixture to a temperature in the range of from about 50° C. to 150° C., at a pressure of about 1 bar (absolute) for a time in the range of about 1 hour to about 50 hours. The mesoporous oxide template can be recovered from the aged mixture, e.g., by centrifuging and washing. Examples of suitable soft templating methods for producing the mesoporous oxide template are disclosed in Q. Liu, et al., Microporous and Mesoporous Materials, 100, 233-240 (2007), which is incorporated by reference herein in its entirety.

A mono-metallic templated precursor is then produced by calcining the mesoporous oxide template, e.g., by exposing the mesoporous oxide template to an oxidant at a temperature ≥350° C. Conventional calcining can be used, such as the calcining disclosed in the Microporous and Mesoporous Materials article, but the invention is not limited thereto.

Following calcination, a multi-metallic templated precursor is produced by depositing a second metal on and/or in the monometallic templated precursor, e.g., on the monometallic templated precursor's external surface and/or in the pores of the monometallic templated precursor. When the first metal is iron, the second metal is typically copper. When the first metal is copper, the second metal is typically iron. In certain aspects, the first metal is iron and the second metal is copper. Typically, the amount of second metal deposited on and/or in the monometallic templated precursor is selected to achieve a molar ratio of first to second metal in the in the range of from 0.1 to 10, e.g., about 0.25 to 4. Conventional methods can be used for impregnating the second metal, e.g., by exposing the monometallic templated precursor to a solution containing nitrate of the second metal, but the invention is not limited thereto. Examples of suitable impregnation methods are disclosed, e.g., in J. L. Cao, et al., J. Mater. Sci., 44, 6663-6669 (2009), which is incorporated by reference herein in its entirety. The multi-metallic templated precursor is calcined, e.g., by exposure to an oxidant at a temperature ≥350° C. Conventional calcining conditions can be used, such as those disclosed in the J. Mater. Chem. An article, the J. Mater. Sci. article, and in the Microporous and Mesoporous Materials article. Typically calcination of iron oxide (e.g., the first and/or second calcination as the case may be) is carried out under conditions to oxidize any $Fe_2O_3$ to $Fe_3O_4$.

In alternative aspects, the synthesis mixture comprises nitrate of the first metal (e.g., iron nitrate) and further comprises nitrate of the second metal (e.g., copper nitrate) and optionally nitrate of the third metal. The relative amount of copper nitrate and iron nitrate is selected to achieve a molar ratio of first to second metal in the multi-metallic templated precursor in the range of from 0.1 to 10, e.g., about 0.25 to 4. Utilizing a synthesis mixture comprising nitrate of the first metal and nitrate of the second metal can simplify catalyst production because the steps for impregnating the second metal and the second calcining are not needed.

Producing the Catalyst from the Calcined Multi-metallic Templated Precursor

The catalyst is produced by reducing the calcined multi-metallic templated precursor. For example, the reduction can be carried out by exposing the calcined multi-metallic templated precursor to a reducing agent (e.g., a reducing gas such as molecular hydrogen and/or syngas) in a reactor vessel such as a tube reactor. Reducing conditions can be conventional conditions for producing macroporous alcohol synthesis catalysts from metal-substituted macroporous metal oxide, but the invention is not limited thereto. In certain aspects, the reduction is carried out under conditions which include exposing the calcined multi-metallic templated precursor to a 1:1 molar mixture of carbon monoxide and molecular hydrogen at a temperature in the range of from 200° C. to 350° C., at a pressure in the range of from 0.5 bar (absolute) to 5 bar (absolute) at a space velocity (GHSV) in the range of from 10 $hr^{-1}$ to 10,000 $hr^{-1}$, for a time in the range of about 1 hour to about 100 hours. Typically, the catalyst is maintained in a reducing environment or an inert environment until the start of the alcohol synthesis reaction. When the maximum temperature achieved by the precursor during calcination is $T_1$, the reduction is typically carried out at a temperature $T_2$, where $T_1$ is $\geq T_2$ and $T_1$-$T_2$ is ≥10° C., e.g., ≥25° C., such as ≥50° C., or ≥75° C.

Process for Producing Lone Chain Alcohol

Certain aspects of the invention relate to a process for catalytically producing long chain alcohol by exposing the specified feed mixture to a catalytically effective amount of the specified catalyst under catalytic long chain alcohol synthesis process conditions. Suitable process conditions will now be described in more detail. The invention is not limited to these process conditions, and this description is not meant to foreclose other process conditions within the broader scope of the invention.

In certain aspects, the reaction is carried out under conditions which include a reaction temperature ≥150° C., a total pressure ≥0.7 MPa (absolute), and a space velocity (GHSV)≥50 $hr^{-1}$. Typically, the reaction conditions include a temperature in the range of from 150° C. to 300° C., e.g., 200° C. to 280° C. In certain aspects, the reaction is carried out at a temperature in the range of from 150° C. to 250° C. Total pressure is typically in the range of from 0.7 MPa to 5 MPa, such as in the range of from 1.0 MPa to 4 Mpa, or 1.5 Mpa to 3.5 MPa. The space velocity (GHSV) is typically in the range of from 100 $hr^{-1}$ to 10,000 $hr^{-1}$, such as in the range of from 500 $hr^{-1}$ to 5000 $hr^{-1}$. The process can be carried out in at least one reaction zone, the reaction zone being located within at least one reactor vessel, e.g., a tube reactor. The catalyst is resistant to deactivation during use, and the process can be operated continuously without interruption for catalyst regeneration, rejuvenation, or replacement for a time ≥10 hours, e.g., ≥100 hours, such as ≥1000 hours, or ≥10,000 hours.

A reaction effluent comprising long chain alcohol is conducted away from the reaction zone. Typically the reaction effluent further comprises any unreacted feed mixture components and byproducts from side reactions such as short chain alcohols. Conventional technology can be utilized for separating the long chain alcohol from the remainder of the reaction effluent, e.g., fractional distillation.

Typically, when operated using the specified feed mixture, the specified catalyst, and the specified operation conditions, the conversion of feed mixture carbon monoxide is ≥45% (weight basis) and the process's selectivity for 1-alcohol is ≥40% (weight basis). Typically, a is ≥0.74, e.g., ≥0.8. In certain aspects, including those where the catalyst includes ordered catalyst produced by soft templating using star surfactant, the process exhibits one or more of (i) total 1-alcohol selectivity ≥40%, e.g., ≥50%; (ii) $C_{2+}$ 1-alcohol selectivity ≥90%, e.g., ≥95%; $C_{6+}$alcohol selectivity ≥50%, e.g., ≥60%, such as ≥70%; $CO_2$ selectivity ≤25%, e.g., ≤10%, such as ≤5%; CO conversion ≥40%, e.g., ≥50%, such as ≥60%; and α≥0.78, e.g., α≥0.80, such as α≥0.85. The methods utilized for determining carbon monoxide conversion, total 1-alcohol selectivity, $C_{2+}$ 1-alcohol selectivity, $C_{6+}$ 1-alcohol selectivity, $CO_2$ selectivity, and a are the same as those disclosed in the ChemCatChem article. The measurements are made at a temperature of 240° C.

The long chain alcohol of the invention is suitable, e.g., for use as and/or in the production of one or more of fuel, lubricating oil, detergent, and plasticizer.

While the present invention has been described and illustrated with respect to certain aspects, it is to be understood that the invention is not limited to the particulars disclosed and extends to all equivalents within the scope of the claims. Unless otherwise stated, all percentages, parts, ratios, etc. are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed. All patents, test procedures, and other documents cited herein, including priority documents, are fully incorporated by reference to the extent such disclosure is not inconsistent and for all jurisdictions in which such incorporation is permitted.

The invention claimed is:

1. A reaction effluent comprising a long chain alcohol produced by the process comprising:
   (a) providing a feed mixture comprising molecular hydrogen and ≥0.01 wt. % of carbon monoxide, the feed mixture having a molecular hydrogen to carbon monoxide molar ratio in the range of from 0.01 to 100;
   (b) providing at least one templated multi-metallic, mesoporous catalyst comprising copper, ≥0.5 wt. % of iron, ≤1.0 wt. % of CuO and ≤1.0 wt. % of $Fe_3O_4$, wherein the templated active material's template is produced from a carbonaceous structure-directing agent, the carbonaceous structure-directing agent comprising one or more of siloxane, urea, and surfactant, the catalyst having
      (i) an iron to copper molar ratio in the range of from 0.1 to 10,
      (ii) a plurality of pores having an average pore size in the range of from 2 nm to 50 nm, and
      (iii) an average surface area ≥50 $m^2/g$; and
   (c) reacting at least a portion of the feed mixture's carbon monoxide and at least a portion of the feed mixture's molecular hydrogen in the presence of the catalyst to produce a reaction effluent comprising long chain alcohol, the reaction conditions including a reaction temperature ≥150° C., a total pressure ≥100 psig, and a space velocity (GHSV) ≥50 $hr^{-1}$,
   wherein the reaction conditions further comprise conversion of 45 wt. % or more of the feed mixture's carbon monoxide, and
   wherein the reaction conditions further comprise a selectivity for formation of 1-alcohol of 40 wt. % or more relative to the weight of converted carbon monoxide.

2. A reaction effluent according to claim 1 further comprising long chain alcohol having an α>0.74, wherein the reaction effluent is formed by a process for conversion of carbon monoxide and molecular hydrogen, the process comprising reaction conditions comprising i) conversion of 45 wt. % or more of carbon monoxide, and ii) a selectivity for formation of 1-alcohol of 40 wt. % or more relative to the weight of converted carbon monoxide.

3. The reaction effluent of claim 2, wherein the long chain alcohol has an α≥0.8.

4. The reaction effluent of claim 1, wherein the reaction conditions comprise a selectivity for formation of $C_{6+}$1-alcohol of 50 wt. % or more relative to the weight of 1-alcohol in the reaction effluent.

5. The reaction effluent of claim 1, wherein the reaction conditions comprise a selectivity for formation of $CO_2$ of 25 wt. % or less relative to the weight of converted carbon monoxide.

6. The reaction effluent of claim 2, wherein the reaction conditions comprise a selectivity for formation of $C_{6+}$1-alcohol of 50 wt. % or more relative to the weight of 1-alcohol in the reaction effluent.

7. The reaction effluent of claim 2, wherein the reaction conditions comprise a selectivity for formation of $CO_2$ of 25 wt. % or less relative to the weight of converted carbon monoxide.

8. The reaction effluent of claim 1, wherein the feed mixture comprises 10 wt. % or more of CO.

* * * * *